United States Patent
Kim et al.

(10) Patent No.: US 12,097,227 B2
(45) Date of Patent: Sep. 24, 2024

(54) **NANOVESICLES DERIVED FROM BACTERIA OF *LACTOCOCCUS* GENUS AND USE THEREOF**

(71) Applicant: MD HEALTHCARE INC., Seoul (KR)

(72) Inventors: Yoon-Keun Kim, Paju-Si (KR); Hae-Sim Park, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 985 days.

(21) Appl. No.: 16/968,058

(22) PCT Filed: Feb. 1, 2019

(86) PCT No.: PCT/KR2019/001439
§ 371 (c)(1),
(2) Date: Aug. 6, 2020

(87) PCT Pub. No.: WO2019/156449
PCT Pub. Date: Aug. 15, 2019

(65) Prior Publication Data
US 2021/0052675 A1  Feb. 25, 2021

(30) Foreign Application Priority Data

Feb. 8, 2018 (KR) .................. 10-2018-0015382
Jan. 31, 2019 (KR) .................. 10-2019-0012758

(51) Int. Cl.
*A61K 35/744* (2015.01)
*A61K 9/00* (2006.01)
*C12Q 1/686* (2018.01)

(52) U.S. Cl.
CPC .......... *A61K 35/744* (2013.01); *A61K 9/0073* (2013.01); *C12Q 1/686* (2013.01); *G01N 2800/2835* (2013.01); *G01N 2800/2871* (2013.01); *G01N 2800/304* (2013.01); *G01N 2800/324* (2013.01); *G01N 2800/326* (2013.01); *G01N 2800/347* (2013.01)

(58) Field of Classification Search
None
See application file for complete search history.

(56) References Cited

U.S. PATENT DOCUMENTS

2017/0327863 A1  11/2017  Apte et al.

FOREIGN PATENT DOCUMENTS

| EP | 3 269 378 A2 | 1/2018 |
|---|---|---|
| EP | 3 275 450 A2 | 1/2018 |
| JP | 2016-525355 A | 8/2016 |
| KR | 10-2016-0073157 A | 6/2016 |
| KR | 10-2016-0110232 A | 9/2016 |
| KR | 10-2017-0015958 A | 2/2017 |
| WO | 2016/141108 A1 | 9/2016 |

OTHER PUBLICATIONS

Slyepchenko et al., "Gut Microbiota, Bacterial Translocation, and Interactions with Diet: Pathophysiological Links between Major Depressive Disorder and Non-Communicable Medical Comorbidities", Psychother. Psychosom., 2017, vol. 86, No. 1, pp. 31-46.
Japanese Office Action dated Oct. 22, 2021 for the corresponding Japanese Patent Application No. 2020-542572, 11 pages.
Choi et al., "Gut microbe-derived extracellular vesicles induce insulin resistance, thereby impairing glucose metabolism in skeletal muscle", Scientific Reports, 2015, 5:15878.
Park et al., "Metagenome Analysis of Bodily Microbiota in a Mouse Model of Alzheimer Disease Using Bacteria-derived Membrane Vesicles in Blood", Experimental Neurobiology, vol. 26, No. 6, Jan. 1, 2017 (Jan. 1, 2017), pp. 369-379, XP055547921.
Extended European Search Report, issued Oct. 13, 2021, for the corresponding EP Patent Application No. 19751779.0, seven pages.

*Primary Examiner* — Brian Gangle
(74) *Attorney, Agent, or Firm* — Vorys, Sater, Seymour and Pease LLP; Mih Suhn Koh

(57) ABSTRACT

Provided are vesicles derived from bacteria of the genus *Lactococcus* and a use thereof, and the inventors experimentally confirmed that the vesicles were significantly reduced in samples obtained from patients with diabetes, myocardial infarction, atrial fibrillation, stroke, renal failure, Parkinson's disease and depression, compared with a normal individual, and the vesicles inhibited the secretion of inflammation mediators caused by pathogenic vesicles. Therefore, it is expected that the vesicles derived from bacteria of the genus *Lactococcus* can be effectively used for a method of diagnosing diabetes, myocardial infarction, atrial fibrillation, stroke, renal failure, Parkinson's disease or depression, and a composition for preventing or treating the disease or inflammatory disease.

4 Claims, 13 Drawing Sheets

Specification includes a Sequence Listing.

NANOVESICLES DERIVED FROM BACTERIA OF *LACTOCOCCUS* GENUS AND USE THEREOF

CROSS-REFERENCE TO RELATED APPLICATIONS

This application is a 371 of PCT/KR2019/001439, filed Feb. 1, 2019, which claims the benefit of priority from Korean Patent Application No. 10-2018-0015382, filed Feb. 8, 2018 and Korean Patent Application No. 10-2019-0012758, filed Jan. 31, 2019, the contents of each of which are incorporated herein by reference in its entirety.

SEQUENCE LISTING

The Sequence Listing submitted in text format (.txt) filed on Aug. 6, 2020, named "SequenceListing.txt", created on Aug. 6, 2020 (845 bytes), is incorporated herein by reference.

TECHNICAL FIELD

The present invention relates to nanovesicles derived from bacteria of the genus *Lactococcus* and a use thereof, and more particularly, to a method of diagnosing a metabolic disease, a cardiovascular disease, renal failure or a neuropsychiatric disease using nanovesicles derived from bacteria of the genus *Lactococcus*, and a composition for preventing or treating the above-mentioned disease or an inflammatory disease.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and the human lifespan. Particularly, metabolic diseases such as diabetes caused by westernization of dietary habits, cardiovascular diseases, such as myocardial infarction and stroke, neuropsychiatric diseases, such as Parkinson's disease, dementia and depression, renal failure, and inflammatory disease are becoming major problems for national health.

Inflammation is a local or systemic protective mechanism against the damage or infection of cells and tissues, and is typically caused by serial biological responses occurring as humoral mediators that constitute the immune system directly response to the damage or infection or stimulate the local or systemic effector system. Examples of a main inflammatory disease include digestive diseases such as gastritis and inflammatory enteritis, oral diseases such as periodontitis, respiratory diseases such as asthma, chronic obstructive pulmonary disease (COPD), and rhinitis, dermatological diseases such as atopic dermatitis, alopecia, and psoriasis, arthritis such as degenerative arthritis and rheumatoid arthritis; and metabolic diseases such as obesity, diabetes, and hepatic cirrhosis.

Chronic inflammation is accompanied by immune dysfunction against an external causative factor. As an immune response against a causative factor derived from bacteria, an immune response of Th17 secreting IL-17 cytokine is important, and when exposed to a bacterial causative factor, neutrophilic inflammation caused by the Th17 immune response occurs. In the process of inflammation, an inflammatory mediator such as TNF-α plays an important role. In addition, it has been recently reported that IL-6 secreted by a bacterial causative factor is involved in not only differentiation to Th17 cells but also the pathogenesis of a cardiovascular disease or brain/neuropsychiatric disease.

Symbiotic microorganisms that live in the human body amount to $10^2$ trillion, which are 10-fold more than human cells, and the number of genes in the microorganisms is known to be over 100 times that of human genes. Microbiota or microbiomes refer to a microbial community including bacteria, archaea and eukarya, present in a given habitat, and it is known that gut microbiota play an important role in a human physiology, and have great effects on human health and diseases due to interaction with human cells.

Bacteria and archaea coexisting in our body secrete nanometer-sized vesicles in order to exchange information on genes, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. It has recently been revealed that pathogenic bacteria-derived vesicles absorbed in our body play an important role in the pathogenesis of metabolic diseases such as diabetes and obesity.

Meanwhile, bacteria of the genus *Lactococcus* are gram-positive bacteria secreting lactic acid. Among these, *Lactococcus lactis* is known as a bacterium critical for the fermentation of dairy products such as cheese, fermented vegetables, and alcoholic beverages. *Lactococcus lactis* may be isolated from materials resulting from milk and plant material fermentation. However, there have been no reports on diagnostic and therapeutic techniques using vesicles derived from bacteria of the genus *Lactococcus* yet.

DISCLOSURE

Technical Problem

As a result of earnest research to solve the conventional problems, the inventors confirmed that the content of vesicles derived from bacteria of the genus *Lactococcus* significantly decreases in samples derived from patients with metabolic diseases such as diabetes, cardiovascular diseases such as myocardial infarction, atrial fibrillation, and stroke, renal failure, and neuropsychiatric diseases such as Parkinson's disease and depression, compared with a normal individual, through metagenomic analysis. In addition, the vesicles derived from bacteria of the genus *Lactococcus* were isolated in vitro, and then their therapeutic efficacy was evaluated, confirming an anti-inflammatory effect. Based on this, the present invention was completed.

Thus, an object of the present invention is to provide a method of providing information for diagnosis of diabetes, myocardial infarction, atrial fibrillation, stroke, renal failure, Parkinson's disease, or depression.

Further, another object of the present invention is to provide a composition for preventing, treating, or alleviating one or more diseases selected from the group consisting of diabetes, myocardial infarction, atrial fibrillation, stroke, renal failure, Parkinson's disease, depression, and inflammatory disease comprising vesicles derived from bacteria of the genus *Lactococcus* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosing diabetes, myocardial infarction, atrial fibrillation, stroke, renal failure, Parkinson's disease, or depression, the method comprising the following steps:
(a) extracting DNAs from extracellular vesicles isolated from samples of a normal individual and a subject;
(b) performing polymerase chain reaction (PCR) on the extracted DNA using a pair of primers prepared based on a gene sequence present in 16S rDNA to obtain each PCR product; and
(c) determining a case in which a content of vesicles derived from bacteria of the genus *Lactococcus* is lower than that of the normal individual sample, as diabetes, myocardial infarction, atrial fibrillation, stroke, renal failure, Parkinson's disease, or depression, through quantitative analysis of the PCR product.

In addition, the present invention provides a method of diagnosing diabetes, myocardial infarction, atrial fibrillation, stroke, renal failure, Parkinson's disease, or depression, the method comprising the following steps:
(a) extracting DNAs from extracellular vesicles isolated from samples of a normal individual and a subject;
(b) performing polymerase chain reaction (PCR) on the extracted DNA using a pair of primers prepared based on a gene sequence present in 16S rDNA to obtain each PCR product; and
(c) determining a case in which a content of vesicles derived from bacteria of the genus *Lactococcus* is lower than that of the normal individual sample, as diabetes, myocardial infarction, atrial fibrillation, stroke, renal failure, Parkinson's disease, or depression, through quantitative analysis of the PCR product.

As an exemplary embodiment of the present invention, the sample in Step (a) may be blood, urine, or saliva.

As another embodiment of the present invention, the primer pair in Step (b) may be primers of SEQ ID Nos. 1 and 2.

Further, the present invention provides a pharmaceutical composition for preventing or treating one or more diseases selected from the group consisting of diabetes, myocardial infarction, atrial fibrillation, stroke, renal failure, Parkinson's disease, depression, and inflammatory disease, comprising vesicles derived from bacteria of the genus *Lactococcus* as an active ingredient.

Further, the present invention provides a food composition for preventing or alleviating one or more diseases selected from the group consisting of diabetes, myocardial infarction, atrial fibrillation, stroke, renal failure, Parkinson's disease, depression, and inflammatory disease, comprising vesicles derived from bacteria of the genus *Lactococcus* as an active ingredient.

Further, the present invention provides an inhalant composition for preventing or treating one or more diseases selected from the group consisting of diabetes, myocardial infarction, atrial fibrillation, stroke, renal failure, Parkinson's disease, depression, and inflammatory disease, comprising vesicles derived from bacteria of the genus *Lactococcus* as an active ingredient.

In one embodiment of the present invention, the inflammatory disease may be one or more selected from the group consisting of atopic dermatitis, acne, psoriasis, sinusitis, rhinitis, conjunctivitis, asthma, dermatitis, an inflammatory collagen vascular disease, glomerulonephritis, encephalitis, inflammatory enteritis, chronic obstructive pulmonary disease, sepsis, septic shock, pulmonary fibrosis, undifferentiated spondylosis, undifferentiated arthrosis, arthritis, inflammatory osteolysis, chronic inflammatory diseases caused by viral or bacterial infections, colitis, ulcerative colitis, inflammatory bowel disease, rheumatoid arthritis, reactive arthritis, osteoarthritis, scleroderma, osteoporosis, atherosclerosis, myocarditis, endocarditis, pericarditis, cystic fibrosis, Hashimoto's thyroiditis, Graves' disease, leprosy, syphilis, Lyme disease, borreliosis, neuroborreliosis, tuberculosis, sarcoidosis, lupus, lupus pernio, lupus tuberculosis, lupus nephritis, systemic lupus erythematosus, macular degeneration, uveitis, irritable bowel syndrome, Crohn's disease, Sjogren's syndrome, fibromyalgia, chronic fatigue syndrome, chronic fatigue immunodeficiency syndrome, myalgic encephalomyelitis, amyotrophic lateral sclerosis, Parkinson's disease, and multiple sclerosis.

In another embodiment of the present invention, the inflammatory disease may be a disease mediated by interleukin-6 (IL-6) or tumor necrosis factor-$\alpha$ (TNF-$\alpha$).

Further, the present invention provides a cosmetic composition for preventing or alleviating inflammatory disease comprising vesicles derived from bacteria of the genus *Lactococcus* as an active ingredient.

In one embodiment of the present invention, the inflammatory disease may be one or more selected from the group consisting of atopic dermatitis, acne, and psoriasis.

Further, the present invention provides a method of preventing or treating one or more diseases selected from the group consisting of diabetes, myocardial infarction, atrial fibrillation, stroke, renal failure, Parkinson's disease, depression, and inflammatory disease, the method comprising a step of administering a pharmaceutical composition comprising vesicles derived from bacteria of the genus *Lactococcus* as an active ingredient to a subject.

Further, the present invention provides a use of vesicles derived from bacteria of the genus *Lactococcus* for preventing or treating one or more diseases selected from the group consisting of diabetes, myocardial infarction, atrial fibrillation, stroke, renal failure, Parkinson's disease, depression, and inflammatory disease.

In one embodiment of the present invention, the vesicles may be derived from *Lactococcus lactis* (*L. lactis*).

In another embodiment of the present invention, the vesicles may have an average diameter of 10 to 200 nm.

In another embodiment of the present invention, the vesicles may be secreted naturally or artificially from bacteria of the genus *Lactococcus*.

Advantageous Effects

The inventors confirmed that intestinal bacteria are not absorbed into the body, but bacteria-derived vesicles are absorbed, systemically distributed and then excreted out of the body through the kidneys, liver and lungs, and by metagenomic analysis for vesicles derived from bacteria present in patients' blood, urine or saliva, also confirmed that vesicles derived from bacteria of the genus *Lactococcus*, which are present in samples obtained from patients with diabetes, myocardial infarction, atrial fibrillation, stroke, renal failure, Parkinson's disease and depression significantly decrease, compared with a normal individual. In addition, when *Lactococcus lactis*, which is one species of bacteria of the genus *Lactococcus*, was cultured in vitro to isolate vesicles, and then the vesicles were administered to inflammatory cells in vitro, it was confirmed that the secretion of inflammation mediators such as IL-6 and TNF-α, mediated by pathogenic vesicles was significantly inhibited. Therefore, it is expected that the vesicles derived from bacteria of the genus *Lactococcus* according to the present invention can be effectively used for a method of diagnosing diabetes, myocardial infarction, atrial fibrillation, stroke, renal failure, Parkinson's disease or depression, and a food or drug composition for preventing or treating the disease or inflammatory disease.

MODES OF THE INVENTION

Figure 1A:
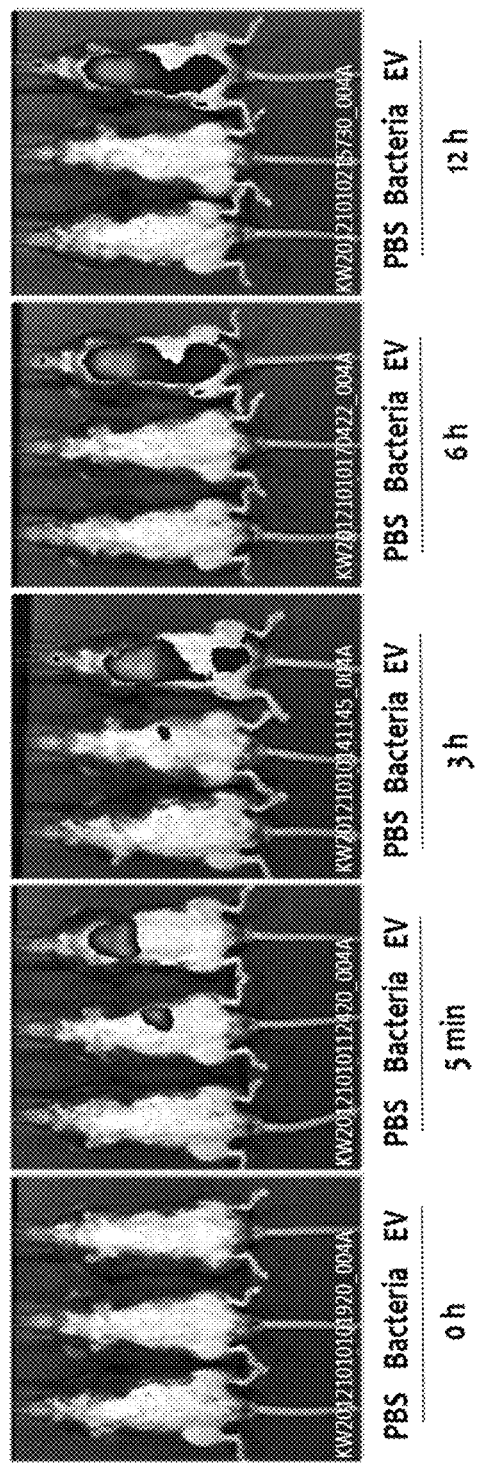
FIG. 1A is a series of photographs capturing distribution patterns of bacteria and bacteria-derived vesicles (EV) by time after the bacteria and the vesicles derived from bacteria were orally administered to mice.

The present invention relates to vesicles derived from bacteria of the genus *Lactococcus* and a use thereof.

The inventors confirmed, through metagenomic analysis, that the content of vesicles derived from bacteria of the genus *Lactococcus* significantly decreases in samples obtained from patients with diabetes, myocardial infarction, atrial fibrillation, stroke, renal failure, Parkinson's disease and depression, compared with a normal individual. Based on this, the present invention was completed.

In the present invention, it was confirmed that the vesicles derived from bacteria of the genus *Lactococcus* are significantly reduced in patients with diabetes, myocardial infarction, atrial fibrillation, stroke, renal failure, Parkinson's disease and depression, compared with a normal individual, and also confirmed that, by identifying characteristics of vesicles isolated from a *Lactococcus lactis* (*L. lactis*) strain, which is one species of bacteria in the genus *Lactococcus*, the vesicles can be used for a composition for preventing or treating the diseases or inflammatory disease.

Thus, the present invention provides a method of providing information for diagnosing diabetes, myocardial infarction, atrial fibrillation, stroke, renal failure, Parkinson's disease, or depression, the method comprising the following steps:

(a) extracting DNAs from extracellular vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) determining a case in which a content of vesicles derived from bacteria of the genus *Lactococcus* is lower than that of the normal individual sample, as diabetes, myocardial infarction, atrial fibrillation, stroke, renal failure, Parkinson's disease, or depression, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether diabetes, myocardial infarction, atrial fibrillation, stroke, renal failure, Parkinson's disease, and depression occur, the level of the disease, and the like.

The term "metabolic disease" used herein refers to a disease accompanied by complications in various organs due to metabolic disorders in the body of a mammal, for example, metabolic disorders such as hyperlipidemia and diabetes, and their complications. In the present invention, the metabolic disease preferably includes diabetes, but the present invention is not limited thereto.

The term "cardiovascular disease" used herein refers to a disease occurring in the cardiovascular system in a mammal, for example, cardiac diseases such as myocardial infarction, cardiomyopathy, angina pectoris and arrhythmia; vasculitis; and cerebrovascular diseases such as dementia and stroke. In the present invention, the cardiovascular disease preferably includes myocardial infarction, atrial fibrillation or stroke, but the present invention is not limited thereto.

The term "neuropsychiatric disease" used herein refers to a disease occurring in the nervous system and the brain of a mammal, for example, brain diseases such as Parkinson's disease and dementia; and metal disorders such as depression, obsessive-compulsive disorder and schizophrenia. In the present invention, the neuropsychiatric disease preferably includes Parkinson's disease or depression, but the present invention is not limited thereto.

The term "inflammatory disease" used herein refers to a disease induced by an inflammatory response in a mammalian body, and in the present invention, the inflammatory disease may be one or more selected from the group consisting of atopic dermatitis, acne, psoriasis, sinusitis, rhinitis, conjunctivitis, asthma, dermatitis, an inflammatory collagen vascular disease, glomerulonephritis, encephalitis, inflammatory enteritis, chronic obstructive pulmonary disease, sepsis, septic shock, pulmonary fibrosis, undifferentiated spondylosis, undifferentiated arthrosis, arthritis, inflammatory osteolysis, chronic inflammatory diseases caused by viral or bacterial infections, colitis, ulcerative colitis, inflammatory bowel disease, rheumatoid arthritis, reactive arthritis, osteoarthritis, scleroderma, osteoporosis, atherosclerosis, myocarditis, endocarditis, pericarditis, cystic fibrosis, Hashimoto's thyroiditis, Graves' disease, leprosy, syphilis, Lyme disease, borreliosis, neuroborreliosis, tuberculosis, sarcoidosis, lupus, lupus pernio, lupus tuberculosis, lupus nephritis, systemic lupus erythematosus, macular degeneration, uveitis, irritable bowel syndrome, Crohn's disease, Sjogren's syndrome, fibromyalgia, chronic fatigue syndrome, chronic fatigue immunodeficiency syndrome, myalgic encephalomyelitis, amyotrophic lateral sclerosis, Parkinson's disease, and multiple sclerosis, but is not limited thereto.

The term "nanovesicle" or "vesicle" refers to a structure formed with a nano-scale membrane, released from various bacteria. Vesicles derived from gram-positive bacteria such as *Lactococcus* include peptidoglycan and lipoteichoic acid, which are components of the bacterial cell wall, and various low-molecular compounds in the vesicle, as well as a protein and a nucleic acid. In the present invention, nanovesicles or vesicles are naturally secreted or artificially produced from bacteria of the genus *Lacotobacillus*, are in the form of a sphere, and have an average diameter of 10 to 200 nm.

The vesicles may be isolated from a culturing solution comprising bacteria of the genus *Lacotobacillus* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample in Step (a) may be blood, urine, or saliva, but is not limited thereto.

In the present invention, the primer pair in Step (b) may be primers of SEQ ID Nos. 1 and 2.

As another aspect of the present invention, the present invention provides a composition for preventing or treating one or more diseases selected from the group consisting of diabetes, myocardial infarction, atrial fibrillation, stroke, renal failure, Parkinson's disease, depression, and inflammatory disease, comprising vesicles derived from bacteria of the genus *Lacotobacillus* as an active ingredient. In the present invention, the composition may include a pharmaceutical composition, an oral composition, oral spray, or an inhalant composition.

As another aspect of the present invention, the present invention provides a food composition for preventing or alleviating one or more diseases selected from the group consisting of diabetes, myocardial infarction, atrial fibrillation, stroke, renal failure, Parkinson's disease, depression, and inflammatory disease, comprising vesicles derived from bacteria of the genus *Lacotobacillus* as an active ingredient.

In the present invention, the inflammatory disease may be a disease mediated by IL-6 or TNF-α, but is not limited thereto.

As another aspect of the present invention, the present invention provides a cosmetic composition for preventing or alleviating inflammatory disease, comprising vesicles derived from bacteria of the genus *Lacotobacillus* as an active ingredient.

In the present invention, the cosmetic composition may be used to prevent or alleviate an inflammatory disease selected from the group consisting of atopic dermatitis, acne and psoriasis, but the present invention is not limited thereto.

The term "prevention" as used herein refers to all actions that suppress diabetes, myocardial infarction, atrial fibrillation, stroke, renal failure, Parkinson's disease, depression, or inflammatory disease or delay the onset thereof via administration of the composition according to the present invention.

The term "treatment" as used herein refers to all actions that alleviate or beneficially change symptoms of diabetes, myocardial infarction, atrial fibrillation, stroke, renal failure, Parkinson's disease, depression, and inflammatory disease via administration of composition according to the present invention.

The term "alleviation" used as used herein refers to all actions that at least reduce a parameter associated with a condition to be treated, for example, the degree of symptoms.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another embodiment of the present invention, metagenomic analysis was performed on saliva of a patient with diabetes and a normal individual. As a result, compared with the saliva of the normal individual, it was confirmed that bacteria of the genus *Lactococcus* and vesicles derived from the bacteria of the genus *Lactococcus* are significantly reduced in the saliva of the patient with diabetes (see Example 3).

In another embodiment of the present invention, metagenomic analysis was performed on blood of a patient with diabetes and a normal individual. As a result, compared with the blood of the normal individual, it was confirmed that vesicles derived from the bacteria of the genus *Lactococcus* are significantly reduced in the blood of the patient with diabetes (see Example 4).

In another embodiment of the present invention, metagenomic analysis was performed on blood of a patient with myocardial infarction and a normal individual. As a result, compared with the blood of the normal individual, it was confirmed that vesicles derived from the bacteria of the genus *Lactococcus* are significantly reduced in the blood of the patient with myocardial infarction (see Example 5).

In another embodiment of the present invention, metagenomic analysis was performed on blood of a patient with atrial fibrillation and a normal individual. As a result, compared with the blood of the normal individual, it was confirmed that vesicles derived from the bacteria of the genus *Lactococcus* are significantly reduced in the blood of the patient with atrial fibrillation (see Example 6).

In another embodiment of the present invention, metagenomic analysis was performed on blood of a patient with stroke and a normal individual. As a result, compared with the blood of the normal individual, it was confirmed that vesicles derived from the bacteria of the genus *Lactococcus* are significantly reduced in the blood of the patient with stroke (see Example 7).

In another embodiment of the present invention, metagenomic analysis was performed on blood of a patient with renal failure and a normal individual. As a result, compared with the blood of the normal individual, it was confirmed that vesicles derived from the bacteria of the genus *Lactococcus* are significantly reduced in the blood of the patient with renal failure (see Example 8).

In another embodiment of the present invention, metagenomic analysis was performed on urine of a patient with Parkinson's disease and a normal individual. As a result, compared with the urine of the normal individual, it was confirmed that vesicles derived from the bacteria of the genus *Lactococcus* are significantly reduced in the urine of the patient with Parkinson's disease (see Example 9).

In another embodiment of the present invention, metagenomic analysis was performed on urine of a patient with depression and a normal individual. As a result, compared with the urine of the normal individual, it was confirmed that vesicles derived from the bacteria of the genus *Lactococcus* are significantly reduced in the urine of the patient with depression (see Example 10).

In another embodiment of the present invention, a *Lactococcus lactis* strain belonging to the genus *Lactococcus* was cultured, and an inflammation-inducing effect of vesicles released from the bacterial cells was evaluated. Macrophages were treated with various concentrations of the *Lactococcus lactis*-derived vesicles, and then with *E. coli*-derived vesicles, which are representative pathogenic vesicles, to make a comparison of the degree of secreting inflammation mediators. As a result, it was seen that, compared with the secretion of IL-6 and TNF-α by *E. coli*-derived vesicles, the secretion capability of the *Lactococcus lactis*-derived vesicles was significantly reduced (see Example 12).

In another embodiment of the present invention, to evaluate an anti-inflammatory effect of vesicles derived from the *Lactococcus lactis* strain, macrophages were treated with various concentrations of the *Lactococcus lactis*-derived vesicles, and then the secretion of inflammation mediators were evaluated, and as a result of evaluating the secretion of inflammation mediators by treating *E. coli*-derived vesicles, which are pathogenic vesicles, it was confirmed that the IL-6 and TNF-α secretion by *E. coli*-derived vesicles are effectively inhibited by the *Lactococcus lactis*-derived vesicles (see Example 13).

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be administered orally or parenterally (e.g., intravenously, subcutaneously, intradermally, intranasally or intratracheally) according to a desired method, and a dose may vary according to the condition and body weight of a patient, the severity of a disease, a drug formulation, an administration route, and duration, but may be suitably selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, an effective amount of the pharmaceutical composition according to the present invention may vary according to a patient's age, gender and body weight, and generally, the pharmaceutical composition may be administered at 0.001 to 150 mg, and preferably, 0.01 to 100 mg per kg of body weight daily or every two days, or 1 to 3 times daily. However, as the dose may be increased or decreased by an administration route, the severity of obesity, gender, a body weight or an age, the above-mentioned dose does not limit the scope of the present invention in any way.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, *stevia* extract, for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

In the inhalant composition of the present invention, the active ingredient may be used as it is or used with other ingredients, and may be suitably used according to a conventional method. A mixing content of the active ingredient may be appropriately determined according to its purpose of use (for prevention or treatment).

The cosmetic composition of the present invention may include ingredients conventionally used in a cosmetic composition as well as vesicles derived from bacteria of the genus *Lactococcus*, and may include, for example, a conventional additive such as an antioxidant, a stabilizer, a solubilizer, a vitamin, a pigment and a flavor, and a carrier.

In addition, the composition of the present invention may also be used by mixing a conventionally used organic sunscreen as long as it does not impair a skin protection effect by reaction with the vesicles derived from bacteria of the genus *Lactococcus*, in addition to vesicles derived from bacteria of the genus *Lactococcus*. The organic sunscreen may be one or more selected from the group consisting of glyceryl PABA, drometrizole trisiloxane, drometrizole, digalloyl trioleate, disodium phenyl dibenzimidazole tetrasulfonate, diethylhexyl butamidotriazone, diethylamino hydroxybenzoyl hexylbenzoate, DEA-methoxycinnamate, a Lawson/dihydroxyacetone mixture, methylenebis-benzotriazolyltetramethylbutylphenol, 4-methylbenzylidene camphor, methyl anthranilate, benzophenone-3(oxybenzone), benzophenone-4, benzophenone-8(dioxyphebenzone), butyl methoxydibenzoylmethane, bisethylhexyloxyphenol methoxyphenyl triazine, cinoxate, ethyl dihydroxypropyl PABA, octocrylene, ethylhexyldimethyl PABA, ethylhexyl methoxycinnamate, ethylhexyl salicylate, ethylhexyl triazone, isoamyl-p-methoxycinnamate, polysilicon-15 (dimethicodiethylbenzal malonate), terephthalylidene dicamphor sulfonic acid and a salt thereof, TEA-salicylate and aminobenzoic acid (PABA).

Products that can contain the cosmetic composition of the present invention include, for example, cosmetics such as an astringent, a skin toner, a nourishing toner, various types of creams, essences, packs and foundations, cleansers, face washes, soaps, treatments, and tonics. Specific formulations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a pressed powder, a loose powder, and an eyeshadow.

MODES OF THE INVENTION

Hereinafter, preferred Examples for helping the understanding of the present invention will be suggested. However, the following Examples are provided only to more easily understand the present invention, and the contents of the present invention are not limited by the following Examples.

EXAMPLES

Example 1. Analysis of In Vivo Absorption, Distribution, and Excretion Patterns of Bacteria and Vesicles Derived from Bacteria In order to evaluate whether intestinal bacteria and bacteria-derived vesicles were systemically absorbed through the gastrointestinal tract, an experiment was performed with the following method. First, a dose of 50 μg of each of fluorescence-labeled intestinal bacteria and intestinal bacteria-derived vesicles was administered through the gastrointestinal tract to the stomach of a mouse, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration (see FIG. 1A).

Figure 1B:
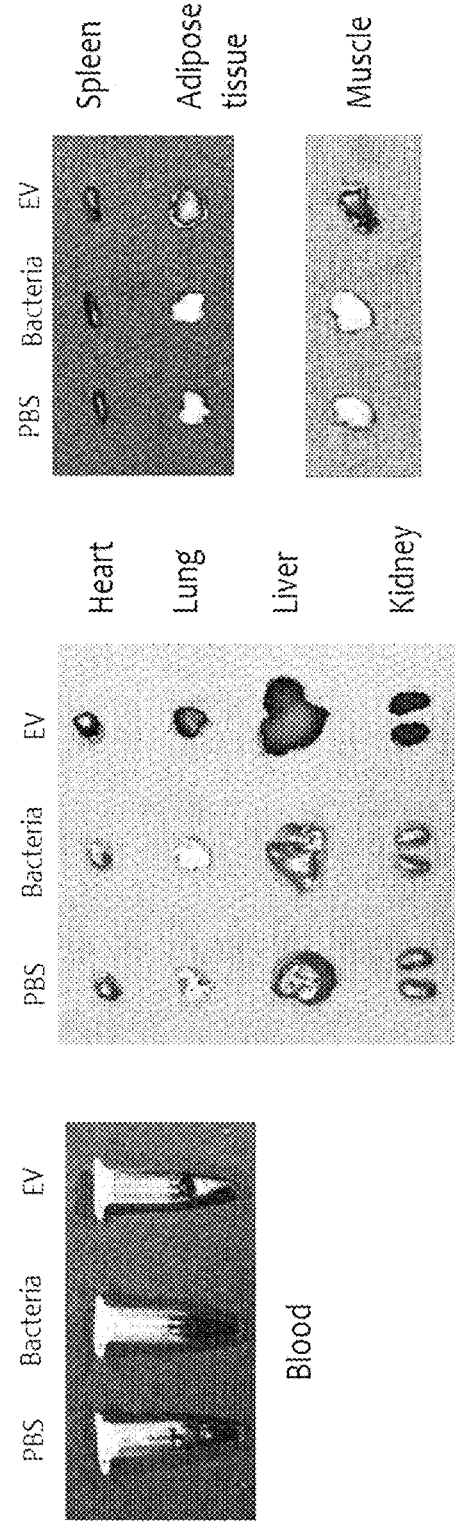
FIG. 1B is a result of evaluating the in vivo distribution patterns of the bacteria and the vesicles by harvesting blood, kidneys, liver, and various organs at 12 hours after orally administering the bacteria and the vesicles.

In order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the blood, heart, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed (see FIG. 1B).

Example 2. Metagenomic Analysis of Vesicles Derived from Bacteria in Clinical Sample After clinical samples such as blood, urine, saliva, and the like was first put into a 10-ml tube and suspended matter was allowed to settle by a centrifuge (3,500×g, 10 min, 4° C.), only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

|  | primer | Sequence | SEQ ID No. |
|---|---|---|---|
| 16S rDNA | 16S_V3_F | 5'-TCGTCGGCAGCGTCAGAT GTGTATAAGAGACAGCCTACG GGNGGCWGCAG-3' | 1 |
|  | 16S_V4_R | 5'-GTCTCGTGGGCTCGGAGA TGTGTATAAGAGACAGGACTA CHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the OTU (operational taxonomy unit) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2:
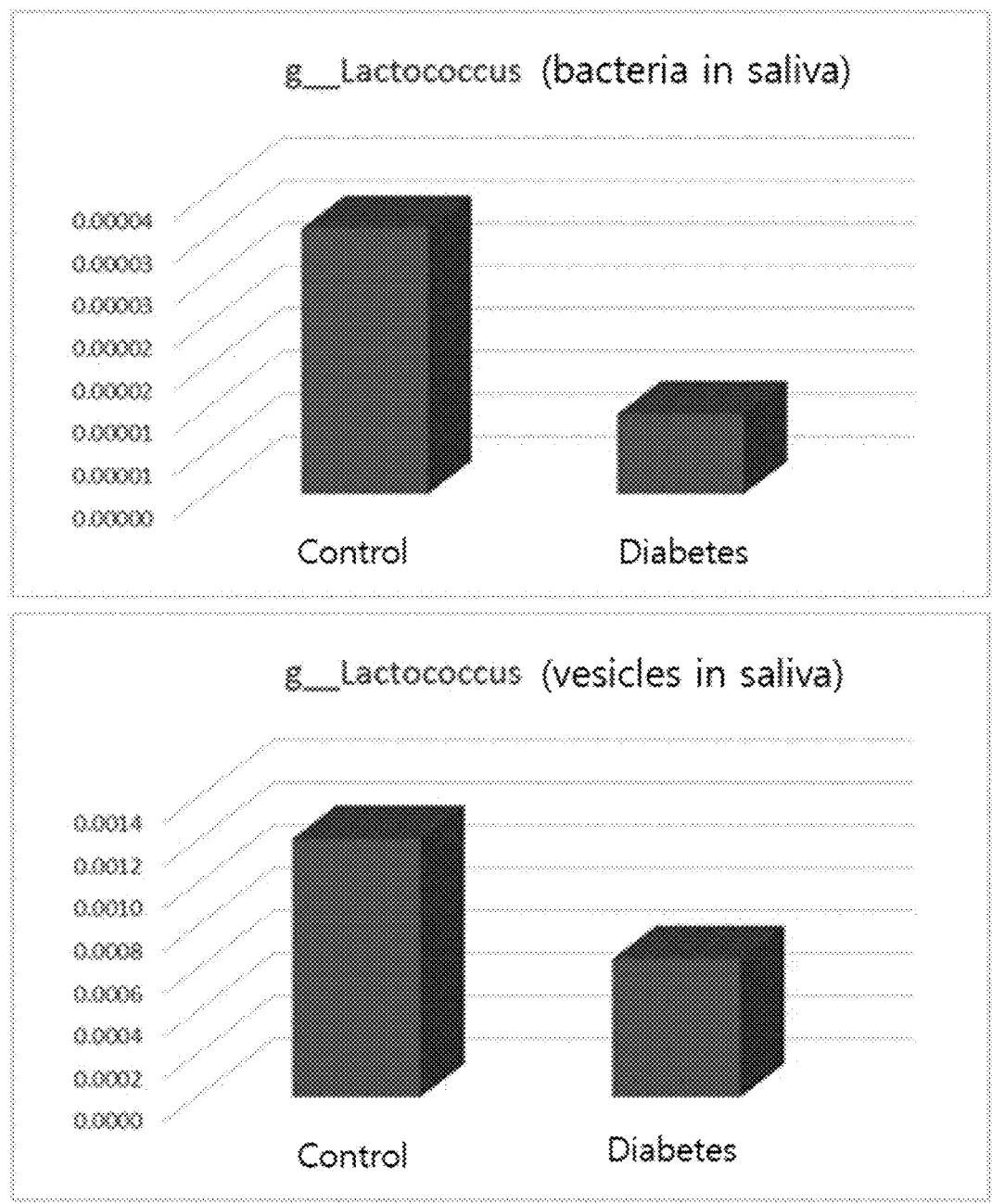
FIG. 2 is a result of comparing the distributions of vesicles derived from bacteria of the genus *Lactococcus* after metagenomic analysis of bacteria and bacteria-derived vesicles present in the saliva of diabetes patients and a normal individual.

Example 3. Metagenomic Analysis of Bacteria and Bacteria-Derived Vesicles in Saliva of Patient with Diabetes and Normal Individual After a metagenomic analysis was performed using the method of Example 2 on the saliva from 47 patients with diabetes, and 277 normal individuals who were matched in age and sex by extracting genes from bacteria and vesicles present in the saliva, the distribution of bacteria of the genus *Lactococcus* and vesicles derived from bacteria of the genus *Lactococcus* was evaluated. As a result, it was confirmed that bacteria of the genus *Lactococcus* and vesicles derived from bacteria of the genus *Lactococcus* were significantly decreased in the saliva from the patients with diabetes as compared to the saliva from the normal individuals (see Table 2, 3, and FIG. 2).

TABLE 2

| Bacteria in saliva | Control | | Diabetes | | t-test | |
|---|---|---|---|---|---|---|
|  | Mean | SD | Mean | SD | p-value | Ratio |
| g_Lactococcus | 0.00003 | 0.00006 | 0.00001 | 0.00002 | 0.00001 | 0.30 |

TABLE 3

| Vesicles in saliva | Control | | Diabetes | | t-test | |
|---|---|---|---|---|---|---|
|  | Mean | SD | Mean | SD | p-value | Ratio |
| g_Lactococcus | 0.0013 | 0.0052 | 0.0006 | 0.0010 | 0.0135 | 0.49 |

Figure 3:
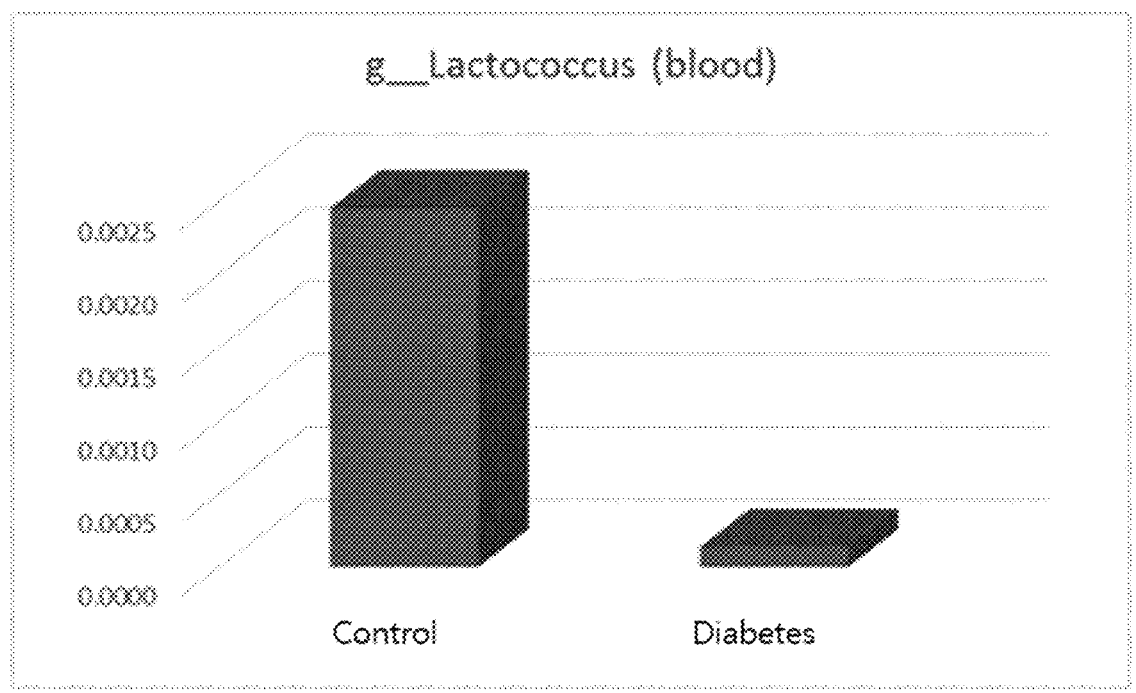
FIG. 3 is a result of comparing the distributions of vesicles derived from bacteria of the genus *Lactococcus* after metagenomic analysis of bacteria-derived vesicles present in the blood of diabetes patients and a normal individual.

Example 4. Metagenomic Analysis of Bacteria-Derived Vesicles in Blood of Patient with Diabetes and Normal Individual After a metagenomic analysis was performed using the method of Example 2 on the blood from 61 patients with diabetes, and 122 normal individuals who were matched in age and sex by extracting genes from vesicles present in the blood, the distribution of vesicles derived from bacteria of the genus *Lactococcus* was evaluated. As a result, it was confirmed that vesicles derived from bacteria of the genus *Lactococcus* were significantly decreased in the blood from the patients with diabetes as compared to the blood from the normal individuals (see Table 4 and FIG. 3).

TABLE 4

| Blood | Control | | Diabetes | | t-test | |
|---|---|---|---|---|---|---|
| | Mean | SD | Mean | SD | p-value | Ratio |
| g__Lactococcus | 0.0025 | 0.0050 | 0.0001 | 0.0002 | <0.0001 | 0.06 |

Figure 4:
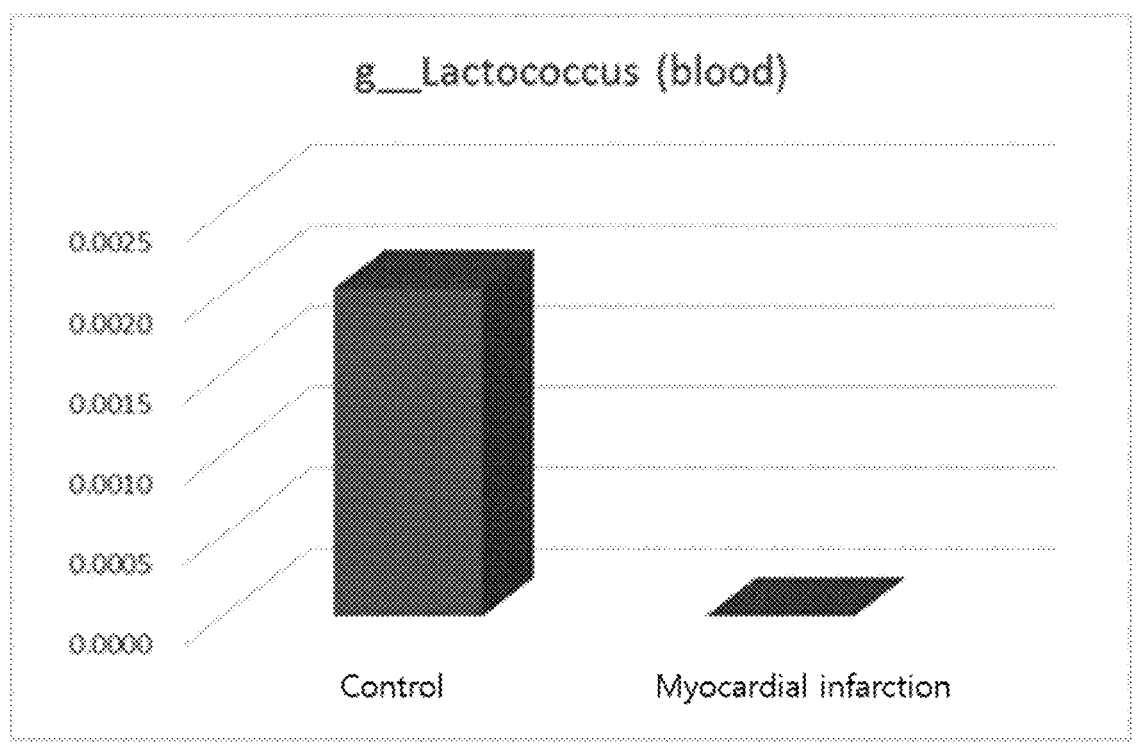
FIG. 4 is a result of comparing the distributions of vesicles derived from bacteria of the genus *Lactococcus* after metagenomic analysis of bacteria-derived vesicles present in the blood of myocardial infarction patients and a normal individual.

Example 5. Metagenomic Analysis of Bacteria-Derived Vesicles in Blood of Patient with Myocardial Infarction and Normal Individual After a metagenomic analysis was performed using the method of Example 2 on the blood from 57 patients with myocardial infarction, and 163 normal individuals who were matched in age and sex by extracting genes from vesicles present in the blood, the distribution of vesicles derived from bacteria of the genus *Lactococcus* was evaluated. As a result, it was confirmed that vesicles derived from bacteria of the genus *Lactococcus* were significantly decreased in the blood from the patients with myocardial infarction as compared to the blood from the normal individuals (see Table 5 and FIG. 4).

TABLE 5

| | Blood | | | | | |
|---|---|---|---|---|---|---|
| | Control | | Myocardial infarction | | t-test | |
| Taxon | Mean | SD | Mean | SD | p-value | Ratio |
| g__Lactococcus | 0.0020 | 0.0038 | 0.0000 | 0.0000 | 0.0001 | 0.00 |

Figure 5:
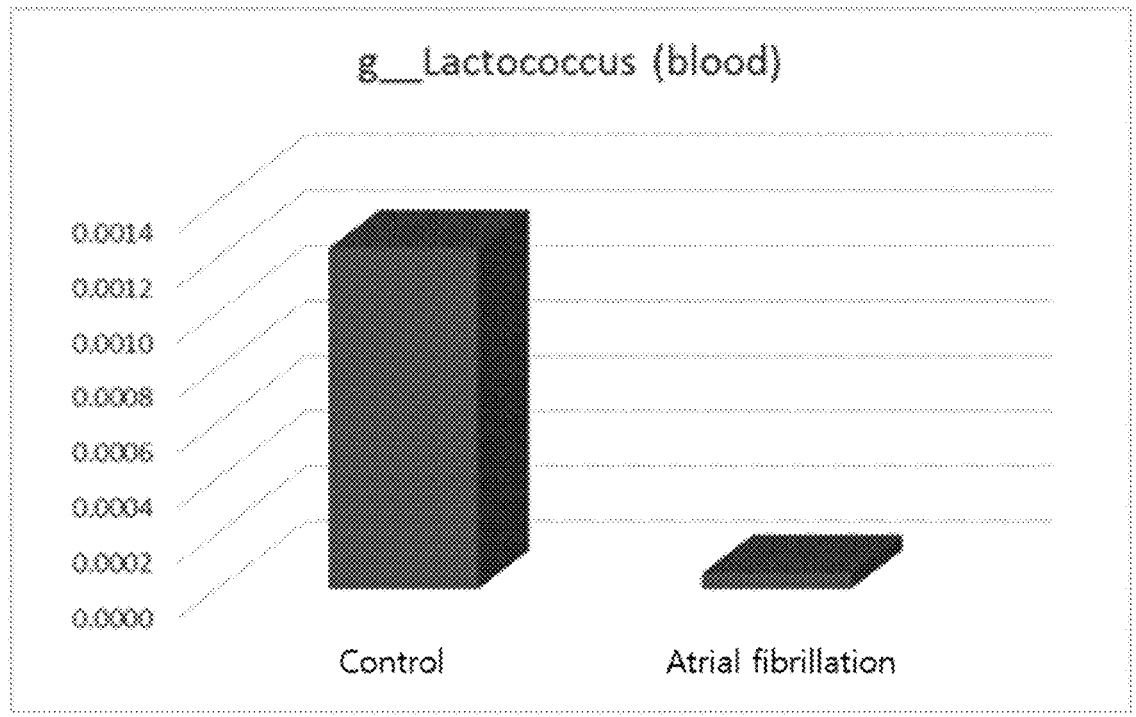
FIG. 5 is a result of comparing the distributions of vesicles derived from bacteria of the genus *Lactococcus* after metagenomic analysis of bacteria-derived vesicles present in the blood of atrial fibrillation patients and a normal individual.

Example 6. Metagenomic Analysis of Bacteria-Derived Vesicles in Blood of Patient with Atrial Fibrillation and Normal Individual After a metagenomic analysis was performed using the method of Example 2 on the blood from 32 patients with atrial fibrillation, and 64 normal individuals who were matched in age and sex by extracting genes from vesicles present in the blood, the distribution of vesicles derived from bacteria of the genus *Lactococcus* was evaluated. As a result, it was confirmed that vesicles derived from bacteria of the genus *Lactococcus* were significantly decreased in the blood from the patients with atrial fibrillation as compared to the blood from the normal individuals (see Table 6 and FIG. 5).

TABLE 6

| | Blood | | | | | |
|---|---|---|---|---|---|---|
| | Control | | Atrial fibrillation | | t-test | |
| Taxon | Mean | SD | Mean | SD | p-value | Ratio |
| g__Lactococcus | 0.0012 | 0.0033 | 0.0001 | 0.0002 | 0.0064 | 0.05 |

Figure 6:
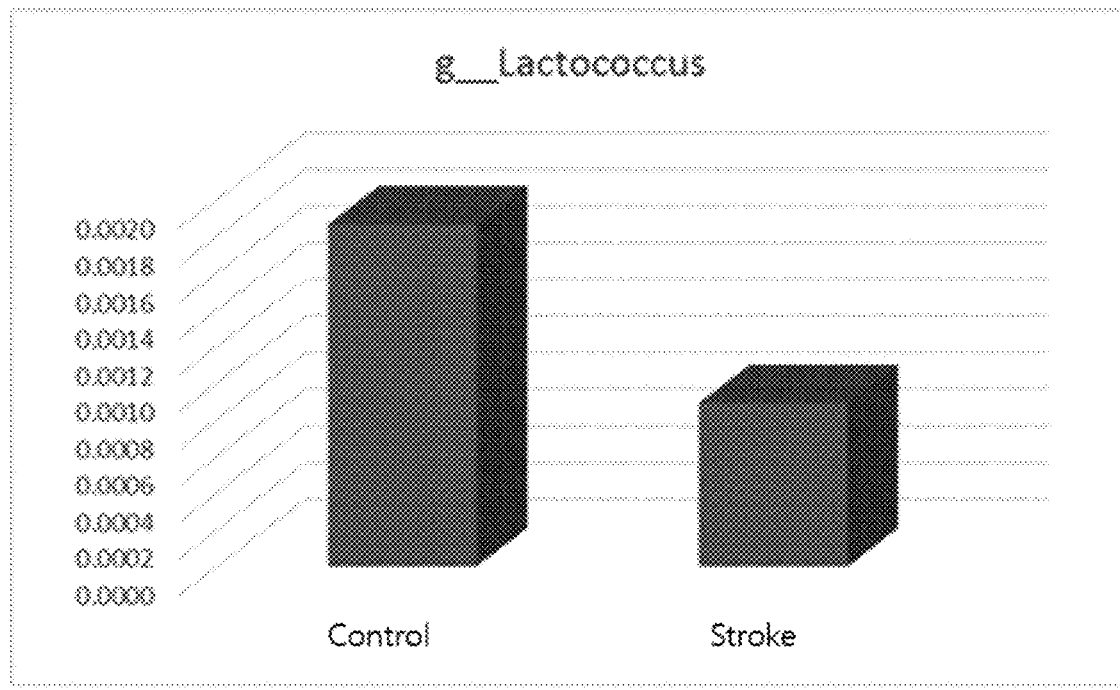
FIG. 6 is a result of comparing the distributions of vesicles derived from bacteria of the genus *Lactococcus* after metagenomic analysis of bacteria-derived vesicles present in the blood of stroke patients and a normal individual.

Example 7. Metagenomic Analysis of Bacteria-Derived Vesicles in Blood of Patient with Stroke and Normal Individual After a metagenomic analysis was performed using the method of Example 2 on the blood from 115 patients with stroke, and 109 normal individuals who were matched in age and sex by extracting genes from vesicles present in the blood, the distribution of vesicles derived from bacteria of the genus *Lactococcus* was evaluated. As a result, it was confirmed that vesicles derived from bacteria of the genus *Lactococcus* were significantly decreased in the blood from the patients with stroke as compared to the blood from the normal individuals (see Table 7 and FIG. 6).

TABLE 7

| | Blood | | | | | |
|---|---|---|---|---|---|---|
| | Control | | Stroke | | t-test | |
| Taxon | Mean | SD | Mean | SD | p-value | Ratio |
| g__Lactococcus | 0.0019 | 0.0048 | 0.0009 | 0.0090 | 0.0318 | 0.48 |

Figure 7:
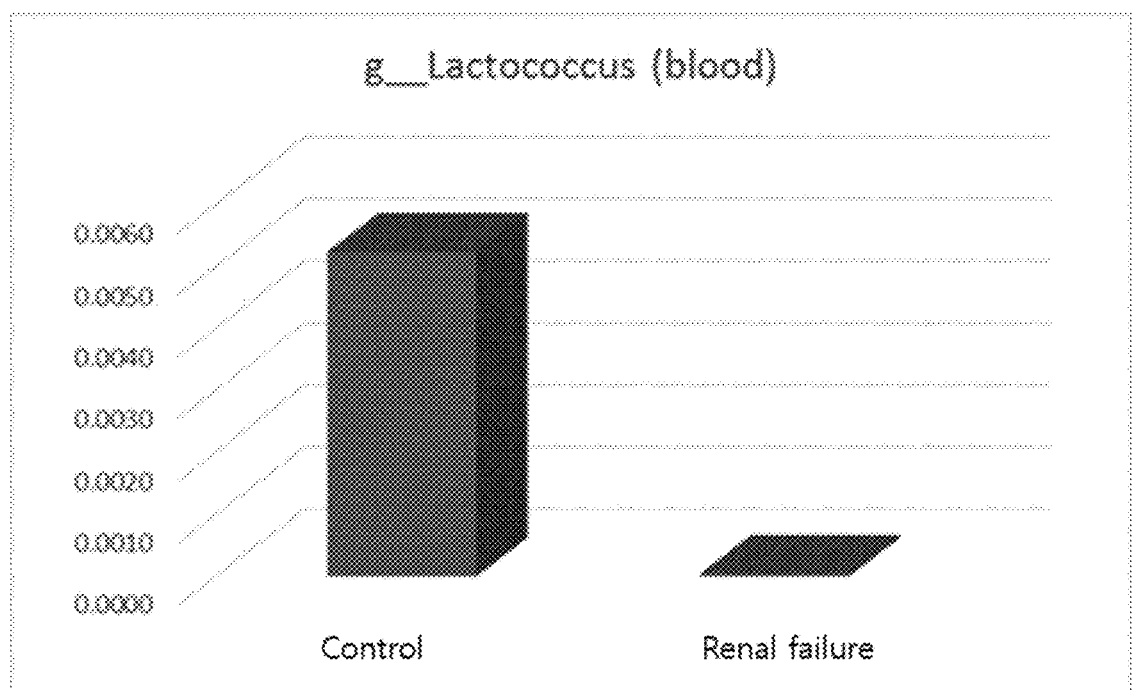
FIG. 7 is a result of comparing the distributions of vesicles derived from bacteria of the genus *Lactococcus* after metagenomic analysis of bacteria-derived vesicles present in the blood of renal failure patients and a normal individual.

Example 8. Metagenomic Analysis of Bacteria-Derived Vesicles in Blood of Patient with Renal Failure and Normal Individual After a metagenomic analysis was performed using the method of Example 2 on the blood from 21 patients with renal failure, and 20 normal individuals who were matched in age and sex by extracting genes from vesicles present in the blood, the distribution of vesicles derived from bacteria of the genus *Lactococcus* was evaluated. As a result, it was confirmed that vesicles derived from bacteria of the genus *Lactococcus* were significantly decreased in the blood from the patients with renal failure as compared to the blood from the normal individuals (see Table 8 and FIG. 7).

TABLE 8

| | Blood | | | | | |
|---|---|---|---|---|---|---|
| | Control | | Renal failure | | t-test | |
| Taxon | Mean | SD | Mean | SD | p-value | Ratio |
| g__Lactococcus | 0.0052 | 0.0081 | 0.0000 | 0.0001 | 0.01 | 0.01 |

Figure 8:
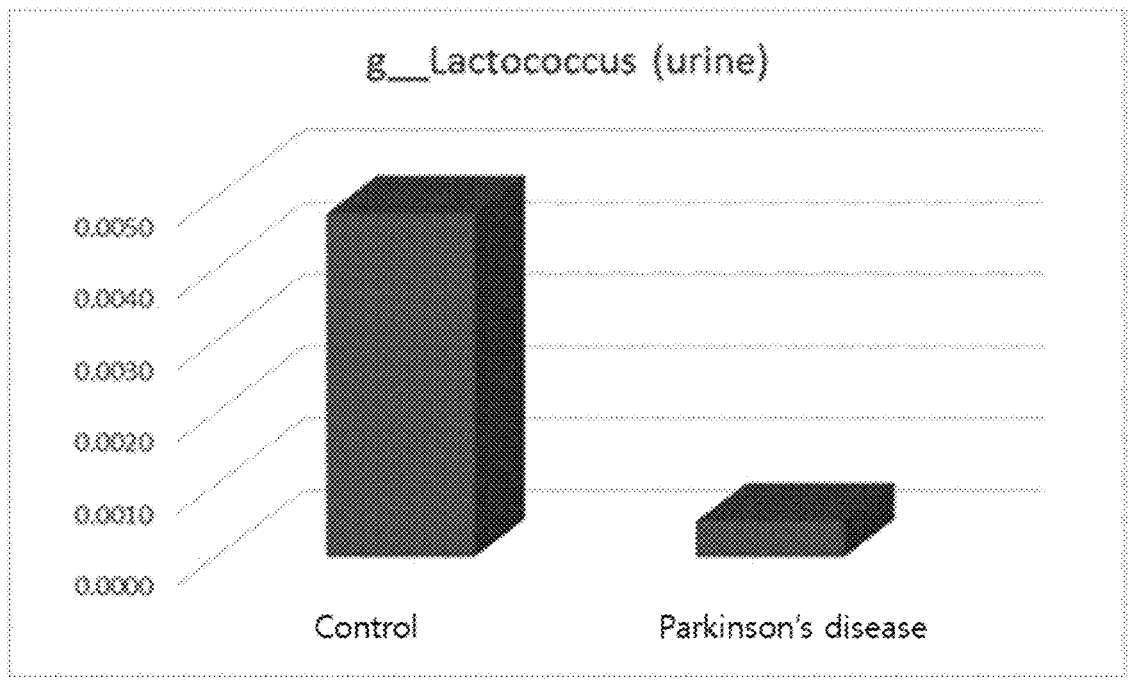
FIG. 8 is a result of comparing the distributions of vesicles derived from bacteria of the genus *Lactococcus* after metagenomic analysis of bacteria-derived vesicles present in the urine of Parkinson's disease patients and a normal individual.

Example 9. Metagenomic Analysis of Bacteria-Derived Vesicles in Urine of Patient with Parkinson's Disease and Normal Individual After a metagenomic analysis was performed using the method of Example 2 on the urine from 39 patients with Parkinson's disease, and 79 normal individuals who were matched in age and sex by extracting genes from vesicles present in the urine, the distribution of vesicles derived from bacteria of the genus *Lactococcus* was evaluated. As a result, it was confirmed that vesicles derived from bacteria of the genus *Lactococcus* were significantly decreased in the urine from the patients with Parkinson's disease as compared to the urine from the normal individuals (see Table 9 and FIG. 8).

TABLE 9

| | Urine | | | | | |
|---|---|---|---|---|---|---|
| | Control | | Parkinson's disease | | t-test | |
| Taxon | Mean | SD | Mean | SD | p-value | Ratio |
| g_Lactococcus | 0.0048 | 0.0064 | 0.0005 | 0.0009 | <0.0001 | 0.10 |

Figure 9:
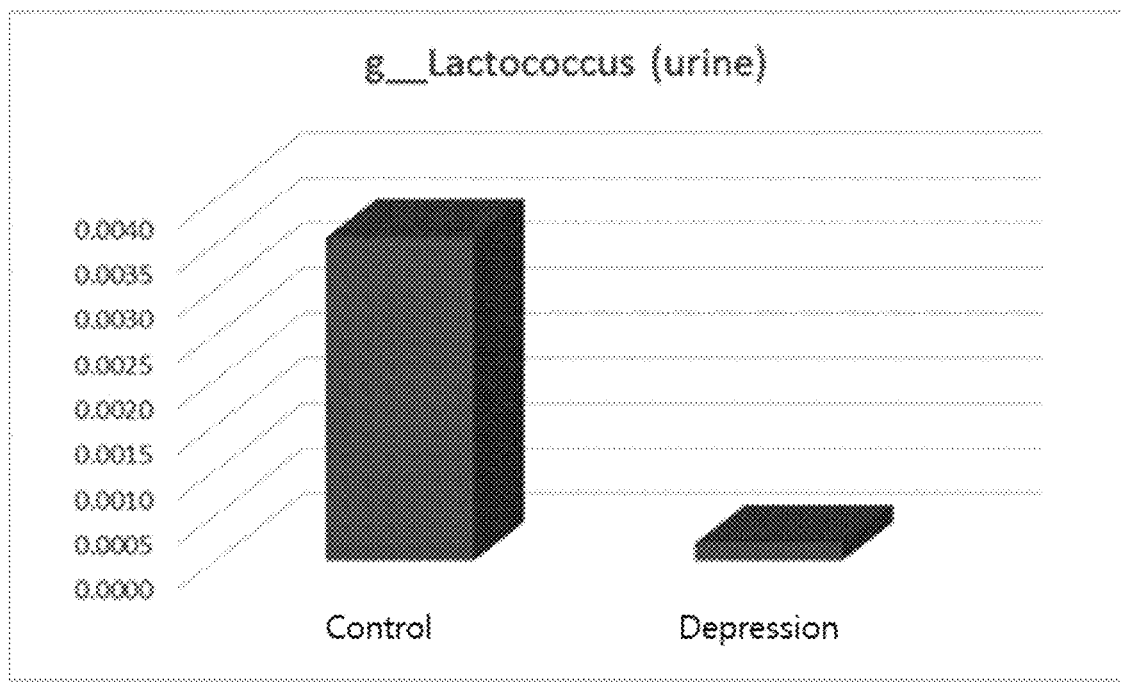
FIG. 9 is a result of comparing the distributions of vesicles derived from bacteria of the genus *Lactococcus* after metagenomic analysis of bacteria-derived vesicles present in the urine of depression patients and a normal individual.

Example 10. Metagenomic Analysis of Bacteria-Derived Vesicles in Urine of Patient with Depression and Normal Individual After a metagenomic analysis was performed using the method of Example 2 on the urine from 20 patients with depression, and 20 normal individuals who were matched in age and sex by extracting genes from vesicles present in the urine, the distribution of vesicles derived from bacteria of the genus *Lactococcus* was evaluated. As a result, it was confirmed that vesicles derived from bacteria of the genus *Lactococcus* were significantly decreased in the urine from the patients with depression as compared to the urine from the normal individuals (see Table 10 and FIG. 9).

TABLE 10

| | Urine | | | | | |
|---|---|---|---|---|---|---|
| | Control | | Depression | | t-test | |
| Taxon | Mean | SD | Mean | SD | p-value | Ratio |
| g_Lactococcus | 0.0036 | 0.0081 | 0.0002 | 0.0002 | 0.04 | 0.05 |

Example 11. Isolation of Vesicles from *Lactococcus lactis* Cell Culture

Based on the above-described examples, the *Lactococcus lactis* strain (*L. lactis*) was cultured, and vesicles isolated therefrom were characterized. The *Lactococcus lactis* strain was cultured in a de Man-Rogosa and Sharpe (MRS) medium until an absorbance (OD 600) reached 1.0 to 1.5 ($OD_{600}$) reached 1.0 to 1.5 at 37° C. under an aerobic condition, and then sub-cultured in a Luria-Bertani (LB) medium. Subsequently, the medium containing the strain was recovered, and then centrifuged at 10,000 g and 4° C. for 20 minutes to remove the strain, followed by filtration through a 0.22 μm filter. The filtered supernatant was concentrated to a volume of 50 mL through a 100 kDa Pellicon 2 Cassette filter membrane (Merck Millipore, US) by microfiltration using a MasterFlex pump system (Cole-Parmer, US). The concentrated supernatant was filtered again using a 0.22 μm filter. Afterward, a protein was quantified by BCA assay, and the following experiment was performed on the obtained vesicles.

Example 12. Inhibition Effect of Inflammation-Inducing of *Lactococcus lactis*-Derived Vesicles To examine the influence of *Lactococcus lactis*-derived vesicles (*L. lactis* EV) on the secretion of inflammation mediators (IL-6 and TNF-α) in inflammatory cells, a mouse macrophage cell line, that is, Raw 264.7 cells, was treated with various concentrations (0.1, 1 and 10 μg/mL) of the *Lactococcus lactis*-derived vesicles, and then cell death was induced, followed by ELISA. More specifically, the Raw 264.7 cells seeded at $4\times10^4$ cells/well in a 48-well cell culture plate were treated with various concentrations of *Lactococcus lactis*-derived vesicles suspended in a serum-free DMEM, and then incubated for 12 hours. Subsequently, cell death was measured using EZ-CYTOX (cell viability, proliferation, cytotoxicity assay kit by Dogen, Korea), the cell culture was collected in a 1.5 ml tube and centrifuged at 3000 g for 5 minutes, and the supernatant was stored at −80° C. for subsequent ELISA.

To perform ELISA, capture antibodies were diluted in PBS, and 50 μL of the resultant dilution was dispensed into a 96 well polystyrene plate according to a working concentration, followed by an overnight reaction at 4° C. Subsequently, the resultant was washed three times with 100 μL of a 0.05% TWEEN® 20 (Polyethylene glycol sorbitan monolaurate) containing PBS (PBST) solution, 100 μL of a 1% BSA-containing PBS (RD) solution was dispensed for blocking at room temperature for 1 hour. 50 μL each of the sample and the standard were dispensed according to a concentration, followed by a reaction at room temperature for 2 hours. The resultant was washed three times with 100 μL of PBST, and detection antibodies were diluted in RD and dispensed at 50 μL according to a working concentration, followed by a reaction at room temperature for 2 hours. The resultant was washed three times with 100 μL of PBST, and Streptavidin-HRP (R&D Systems, USA) was diluted in RD at 1/40 and dispensed at 50 μL, followed by a reaction at room temperature for 20 minutes. Finally, the resultant was washed three times with 100 μL of PBST, 50 μL of a TMB substrate (SurModics, USA) was dispensed, and when color development progressed for 5 to 20 minutes, 50 μL of a 1M sulfuric acid solution was dispensed to stop the reaction, and then absorbance was measured at 450 nm using a SpectraMax M3 microplate reader (Molecular Devices, USA).

Figure 10:
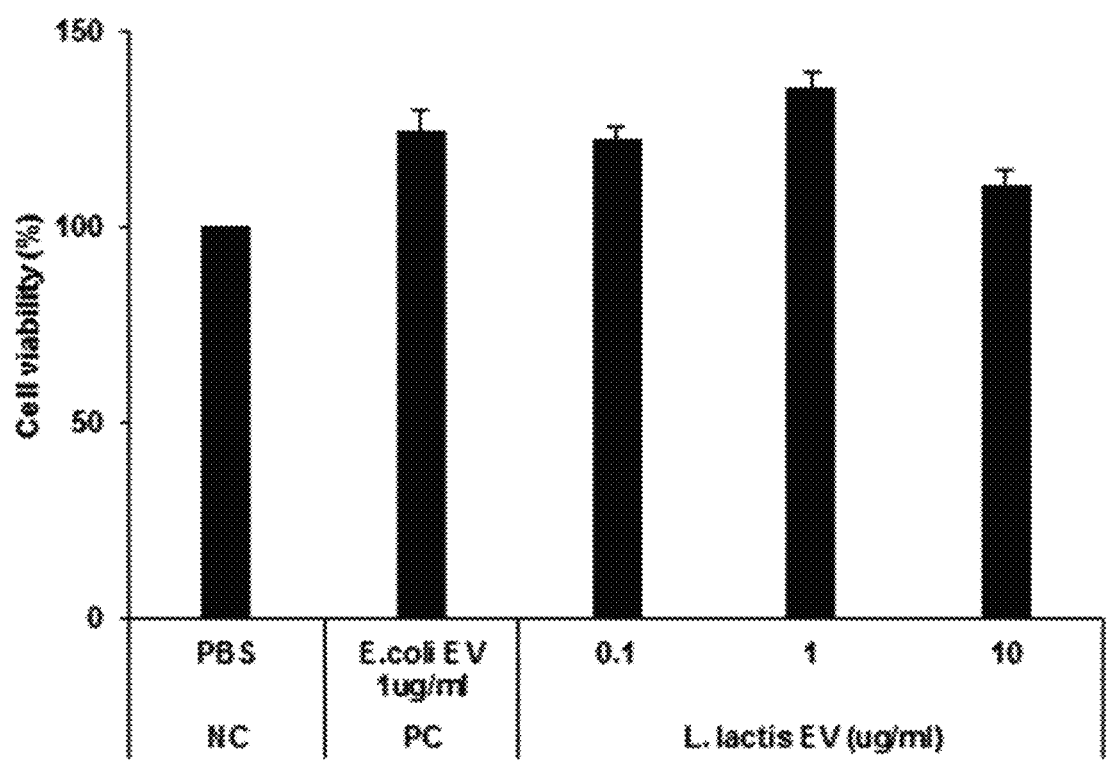
FIG. 10 is a result obtained by evaluating cell death by treating macrophages (Raw264.7 cells) with *Lactococcus lactis*-derived vesicles to evaluate a cell death effect of *Lactococcus lactis*-derived vesicles.
Figure 11:
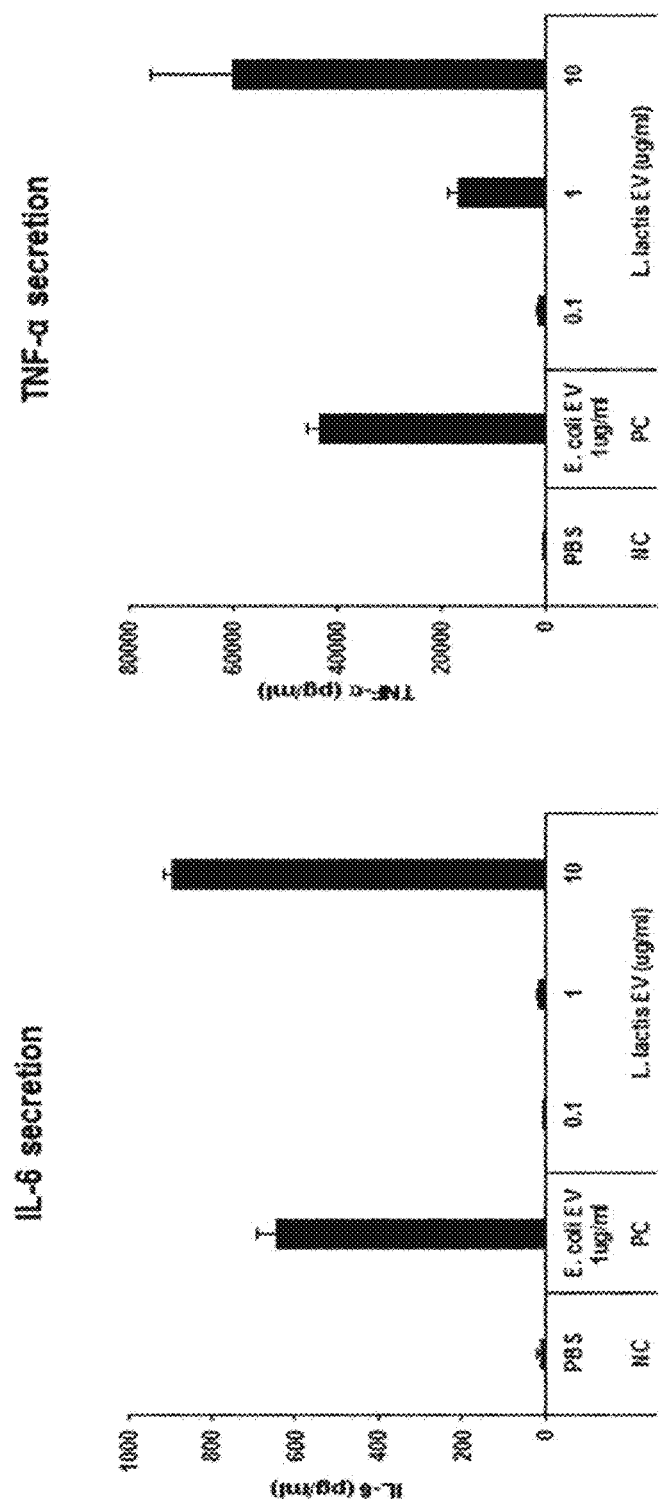
FIG. 11 is a result of comparing the degree of secretion of inflammation mediators such as IL-6 and TNF-α with pathogenic vesicles (*E. coli* EV) by treating macrophages (Raw264.7 cells) with *Lactococcus*-derived vesicles to evaluate an inflammation-inducing effect of *Lactococcus lactis*-derived vesicles.

As a result, as shown in FIG. 10, cell death of the inflammatory cells, caused by the treatment of the *Lactococcus lactis*-derived vesicles, was not induced. In addition, it was confirmed that the secretion of the inflammation mediators (IL-6 and TNF-α) from the mouse macrophage cell line, caused by the treatment of 0.1 and 1 μg/mL of the *Lactococcus lactis*-derived vesicles was significantly reduced, compared with pathogenic vesicles, that is, *E. coli*-derived vesicles (*E. coli* EV) (see FIG. 11).

Figure 12:
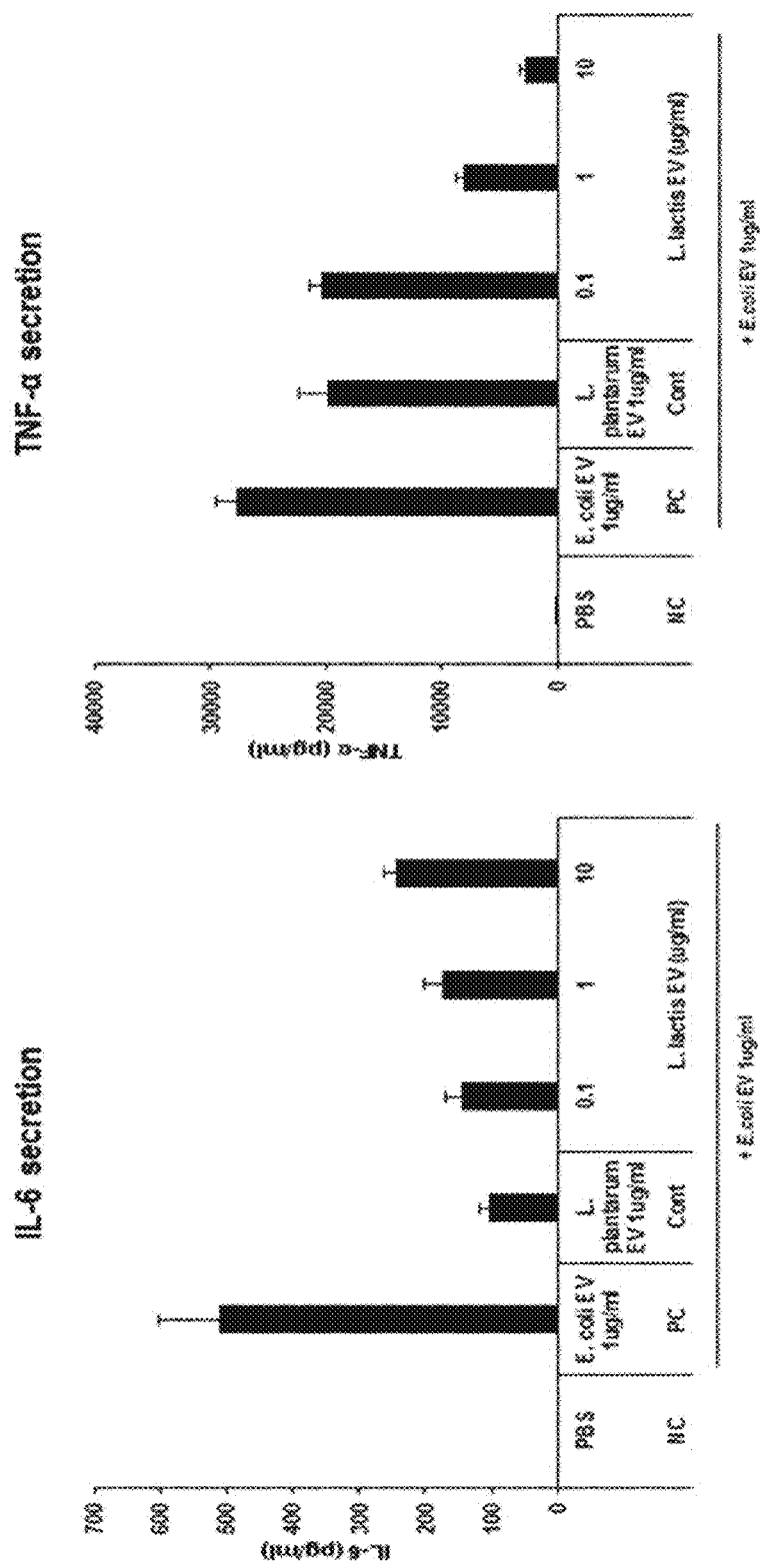
FIG. 12 is a result of evaluating an effect of *Lactococcus lactis*-derived vesicles on the secretion of IL-6 and TNF-α, which are inflammatory mediators, by *E. coli* vesicles, after pretreatment of *Lactococcus*-derived vesicles prior to treatment with *E. coli* EVs, which are pathogenic vesicles, to evaluate an effect of *Lactococcus lactis*-derived vesicles on anti-inflammation.

Example 13. Anti-Inflammatory Effects of *Lactococcus lactis*-Derived Vesicles Based on the above results, to evaluate the anti-inflammatory effect of the *Lactococcus lactis*-derived vesicles, the mouse macrophage cell line was pre-treated with various concentrations (0.1, 1 and 10 μg/mL) of the *Lactococcus lactis*-derived vesicles for 12 hours, and then treated with 1 μg/mL of the pathogenic vesicles, that is, *E. coli*-derived vesicles, and after 12 hours, the secretion of inflammatory cytokines was measured by ELISA. As a result, it was confirmed that, when the *Lactococcus lactis*-derived vesicles were pre-treated, the secretion of IL-6 and TNF-α by *E. coli*-derived vesicles was significantly inhibited (see FIG. 12). Particularly, the effect of inhibiting TNF-α secretion caused by the pretreatment of the *Lactococcus lactis*-derived vesicles is greater than that caused by the pretreatment of *Lactobacillus plantarum*-derived vesicles, which are an effective microorganism control (see FIG. 12). This result shows that inflammatory responses induced by pathogenic vesicles such as *E. coli*-derived vesicles can be effectively inhibited by the *Lactococcus lactis*-derived vesicles.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Vesicles derived from bacteria of the genus *Lactococcus* according to the present invention is expected to be effectively used for a method of diagnosing diabetes, myocardial infarction, atrial fibrillation, stroke, renal failure, Parkinson's disease, and depression, and a food or drug composition for preventing or treating the above-mentioned diseases or an inflammatory disease.

The invention claimed is:

1. A method of alleviating or treating inflammatory disease, the method comprising administering to a subject in need thereof a composition comprising an effective amount of vesicles derived from *Lactococcus lactis*,
   wherein the inflammatory disease is mediated by interleukin-6 (IL-6) or tumor necrosis factor-α (TNF-α).

2. The method of claim 1, wherein the vesicles have an average diameter of 10 to 200 nm.

3. The method of claim 1, wherein the composition is a pharmaceutical composition, a food composition, or a cosmetic composition.

4. The method of claim 1, wherein the composition is an inhalant composition.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a or g or c or t/u

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc      55
```